(12) United States Patent
Watson et al.

(10) Patent No.: US 11,712,319 B2
(45) Date of Patent: Aug. 1, 2023

(54) 360 DEGREES PLUS ROTATION CAMERA MODULE FOR SURGICAL LIGHT HEAD HANDLE

(71) Applicant: American Sterilizer Company, Mentor, OH (US)

(72) Inventors: Breese J. Watson, Rocky River, OH (US); Gregory Turcovsky, Mentor, OH (US)

(73) Assignee: American Sterilizer Company, Mentor, OH (US)

( * ) Notice: Subject to any disclaimer, the term of this patent is extended or adjusted under 35 U.S.C. 154(b) by 190 days.

(21) Appl. No.: 17/208,126

(22) Filed: Mar. 22, 2021

(65) Prior Publication Data

US 2021/0302808 A1   Sep. 30, 2021

Related U.S. Application Data

(60) Provisional application No. 63/000,655, filed on Mar. 27, 2020, provisional application No. 63/000,672, (Continued)

(51) Int. Cl.
*G03B 17/56* (2021.01)
*F21V 33/00* (2006.01)
(Continued)

(52) U.S. Cl.
CPC .......... *A61B 90/30* (2016.02); *A61B 90/361* (2016.02); *A61B 90/37* (2016.02);
(Continued)

(58) Field of Classification Search
USPC ............ 396/4, 428; 600/249; 362/572, 573; 248/187.1
See application file for complete search history.

(56) References Cited

U.S. PATENT DOCUMENTS 3,405,562 A   10/1968   Brandt
4,566,295 A   1/1986   Mason
(Continued)

OTHER PUBLICATIONS

Stryker Visum Surgical Lights & StrykeCam In-Light Camera, Operations and Maintenance Manual, Apr. 2016.*
(Continued)

*Primary Examiner* — Clayton E. LaBalle
*Assistant Examiner* — Warren K Fenwick
(74) *Attorney, Agent, or Firm* — Renner, Otto, Boisselle & Sklar, LLP

(57) ABSTRACT

A surgical lighting system and a method of rotating a camera of a surgical lighting system includes a light head housing including a plurality of light emitting elements arranged to emit light downward to a region of interest, a handle mounted to and protruding downward from the light head housing, the handle including a handle housing having a sufficient size to be gripped by the human hand, and a camera assembly mounted within the handle housing and including a camera having a field of view that encompasses at least a portion of the region of interest. The camera assembly is mounted within the handle housing for rotation greater than 360 degrees about a rotation axis from a first stop to a second stop and vice versa. The first stop limits clockwise rotation of the camera and the second stop limits counterclockwise rotation of the camera.

26 Claims, 10 Drawing Sheets

Related U.S. Application Data filed on Mar. 27, 2020, provisional application No. 63/000,719, filed on Mar. 27, 2020.

(51) Int. Cl.

| | | |
|---|---|---|
| *G03B 15/14* | (2021.01) | |
| *A61B 90/30* | (2016.01) | |
| *A61B 90/00* | (2016.01) | |
| *G02B 6/38* | (2006.01) | |
| *G03B 30/00* | (2021.01) | |
| *A61B 90/35* | (2016.01) | |
| *F21W 131/205* | (2006.01) | |
| *A61B 90/50* | (2016.01) | |

(52) U.S. Cl.
CPC ........ *F21V 33/0052* (2013.01); *G02B 6/3885* (2013.01); *G03B 15/14* (2013.01); *G03B 17/561* (2013.01); *G03B 30/00* (2021.01); *A61B 90/35* (2016.02); *A61B 2090/306* (2016.02); *A61B 2090/308* (2016.02); *A61B 2090/5025* (2016.02); *F21W 2131/205* (2013.01)

(56) References Cited

U.S. PATENT DOCUMENTS

| | | | |
|---|---|---|---|
| 5,326,075 A | 7/1994 | Goff | |
| 6,633,328 B1 | 10/2003 | Byrd et al. | |
| 6,909,465 B2 | 7/2005 | Liang | |
| 8,066,413 B2 | 11/2011 | Czech et al. | |
| 8,289,682 B2* | 10/2012 | Origuchi | F16M 11/18 396/419 |
| 8,424,406 B2 | 4/2013 | Wintsch et al. | |
| 8,734,140 B2 | 5/2014 | Wilton et al. | |
| 9,145,924 B2 | 9/2015 | Baba et al. | |
| 9,737,452 B2 | 8/2017 | Lubbers et al. | |
| 10,352,419 B2 | 7/2019 | Brown et al. | |
| 2004/0047623 A1* | 3/2004 | Top | G08B 13/19619 396/427 |
| 2011/0243547 A1* | 10/2011 | Khamsepoor | H04N 5/2251 396/428 |
| 2015/0184779 A1* | 7/2015 | Timoszyk | A61B 90/30 285/282 |
| 2016/0097518 A1 | 4/2016 | Kim et al. | |
| 2016/0230974 A1 | 8/2016 | Timoszyk et al. | |

OTHER PUBLICATIONS

Manual 360 Rotation Stage with Two Hard Stops; Product Brochure; THORLABS; copyright 1999-2019.

Stryker Visum Surgical Lights & StrykeCam In-Light Camera; Stryker Operations and Maintenance Manual; dated Apr. 2016.

Trumpf Medical; iLED Surgical Light; date unknown, downloaded Oct. 7, 2019.

International Search Report and Written Opinion for corresponding PCT International Application PCT/US2021/023421, dated Jul. 16, 2021.

\* cited by examiner

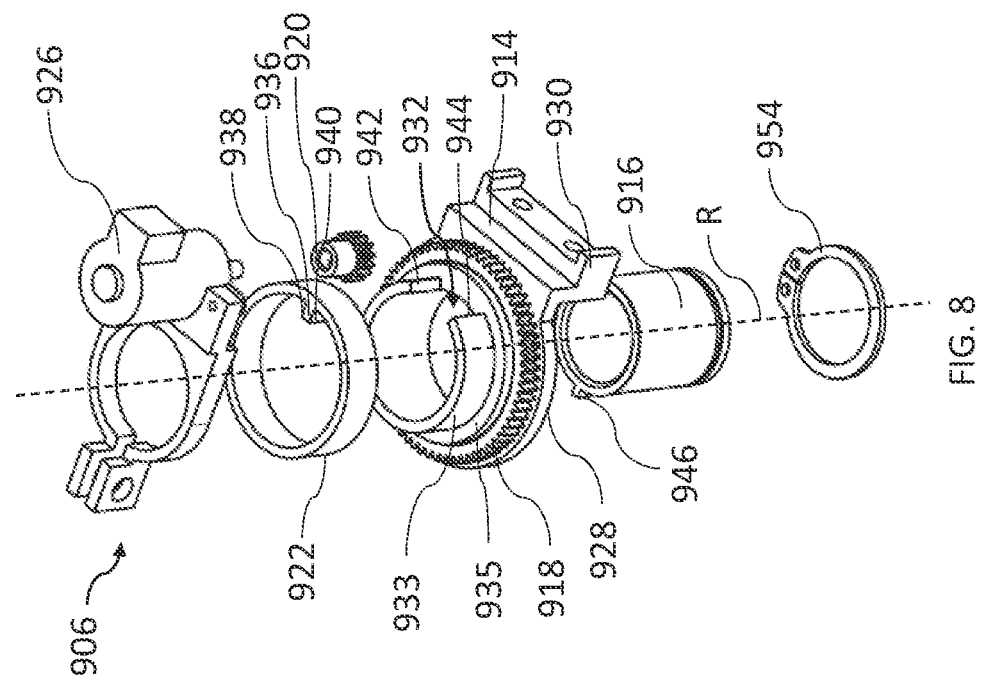
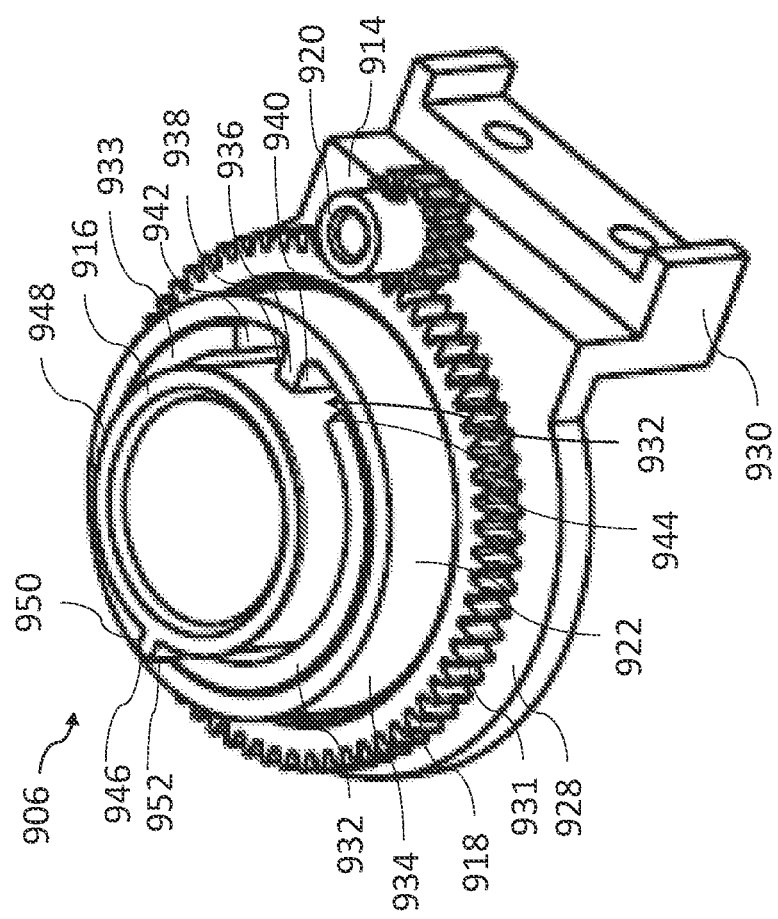

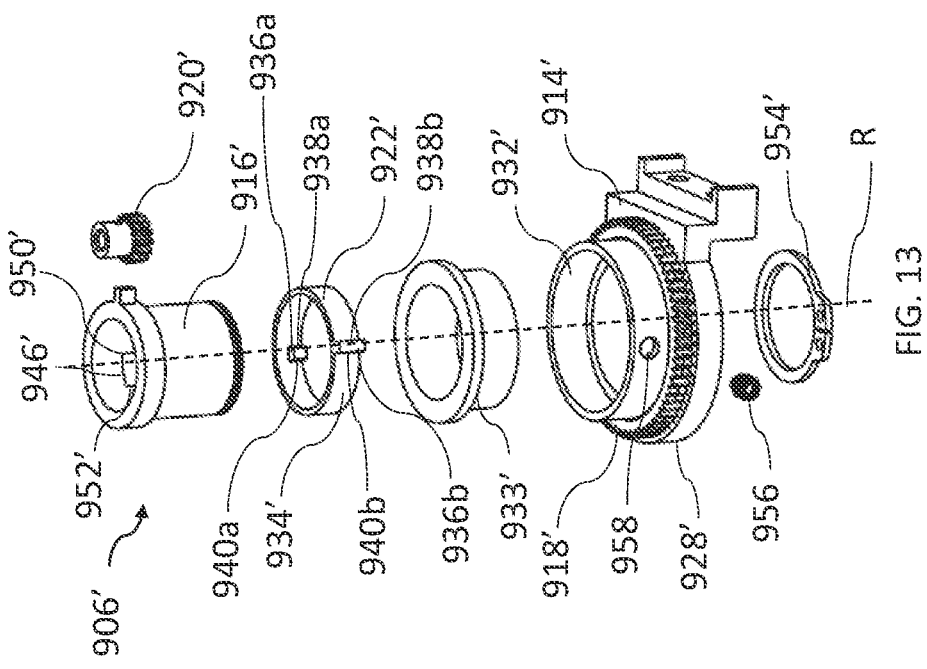
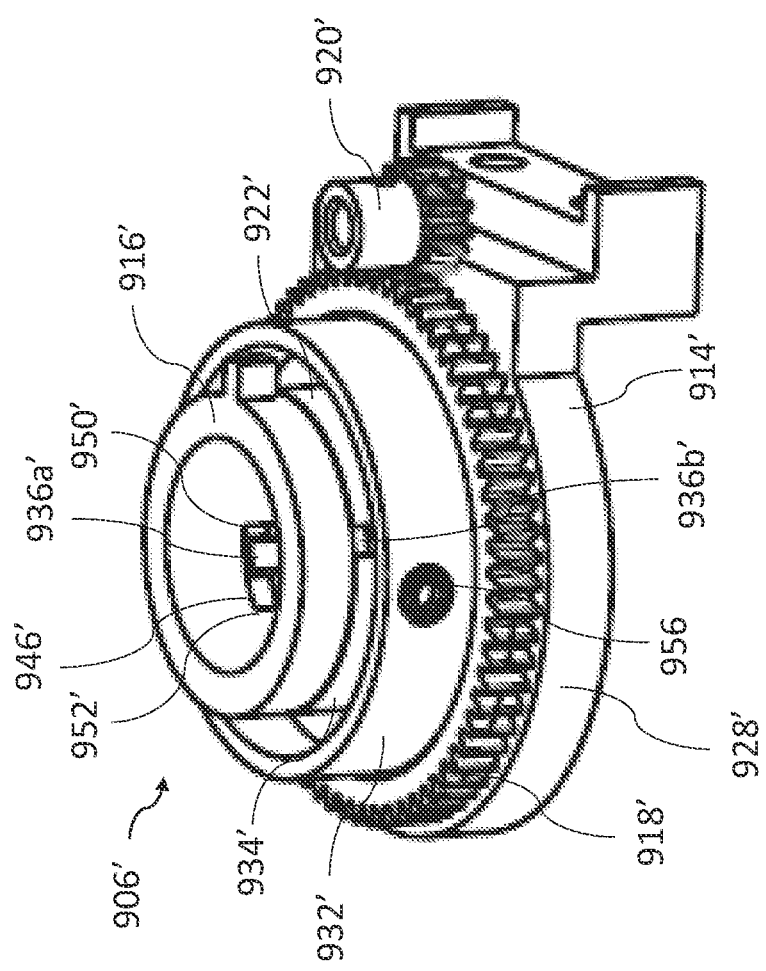
FIG. 13
FIG. 12

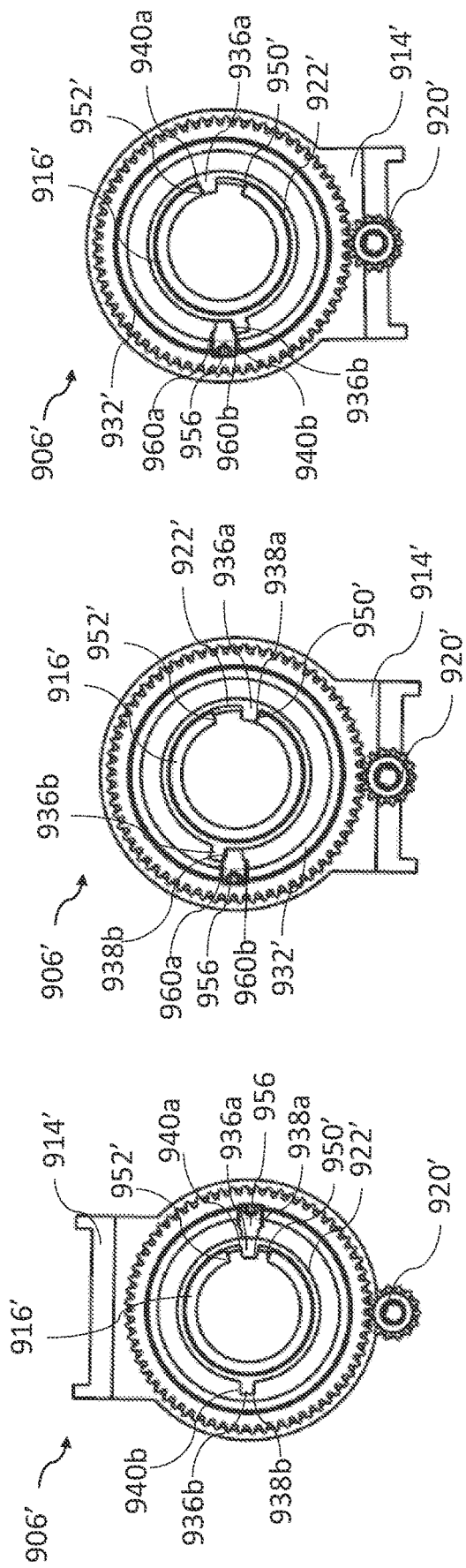

360 DEGREES PLUS ROTATION CAMERA MODULE FOR SURGICAL LIGHT HEAD HANDLE

This application claims priority to U.S. Patent Application No. 63/000,655 filed Mar. 27, 2020; U.S. Patent Application No. 63/000,672 filed Mar. 27, 2020; and U.S. Patent Application No. 63/000,719 filed Mar. 27, 2020. These prior applications are incorporated herein by reference.

FIELD OF INVENTION

This application relates generally to a camera assembly for a surgical light, and more particularly to a camera assembly that is mounted for rotation in a handle of a surgical light.

BACKGROUND

Surgical lights are used in operating rooms to provide increased light to a specific area of the room. For example, the surgical light may be positioned in an operating room and configured to provide increased light to a specific area of a surgical patient. The light may include a light head housing containing a light source, a handle mounted to the light head housing for manual operation by a human hand, and a camera assembly that is mounted in the handle and configured to capture images in a region of interest formed by the light source directing light to an area below the light head housing. The handle is typically formed to have an ergonomic structure that enables a user to wrap a hand around the handle such that the internal space within the handle is limited.

In order to capture a particular image at a proper orientation, the camera assembly may be rotated which reduces the need to reposition the light source. Prior attempts at providing camera rotation mechanisms are deficient in that the prior attempts include using bulky arrangements that require a large amount of space for accommodating the rotational movement and rotation limiting stops, such that the handle may be unable to accommodate the rotation mechanism. Still another disadvantage of the prior mechanisms is that the components may have large protrusions that interfere with wiring or cables required for operation of the surgical light.

SUMMARY OF INVENTION

According to one aspect of the invention, a surgical lighting system includes a light head housing including a plurality of light emitting elements therein that are arranged to emit light downward to a region of interest; a handle mounted to the light head housing and protruding downward from the light head housing, the handle including a handle housing having a sufficient size to be gripped by the human hand; and, a camera assembly mounted within the handle housing, the camera assembly including a camera having a field of view that encompasses at least a portion of the region of interest; wherein the camera assembly is mounted within the handle housing for rotation greater than 360 degrees about a rotation axis from a first stop to a second stop and vice versa, wherein the first stop limits clockwise rotation of the camera about the rotation axis and the second stop limits counterclockwise rotation of the camera about the rotation axis.

Embodiments of the invention may include one or more of the following additional features separately or in combination.

The first and second stops may lie in a plane situated between the light head housing and the camera.

The camera assembly may include a bracket that is rotatably mounted to a spindle fixed relative to the handle housing.

The surgical lighting system may include a free rotating ring that is rotatable about the rotation axis and movable relative to the bracket and movable relative to the spindle.

The rotation greater than 360 degrees may be a compound of a first rotation range and a second rotation range, the first rotation range defined by the camera assembly engaging first and second contact faces of the free rotating ring, the second rotation range defined by a protruding portion of the free rotating ring engaging first and second contact faces of the spindle.

The first stop may include the camera assembly engaging the first contact face of the free rotating ring, and the protruding portion of the free rotating ring engaging the first contact face of the spindle.

The second stop may include the camera assembly engaging the second contact face of the free rotating ring, and the protruding portion of the free rotating ring engaging the second contact face of the spindle.

The bracket of the camera assembly may include an arcuate cutout, and the first rotation range may be defined by opposite faces of the arcuate cutout engaging the respective first and second contact faces of the free rotating ring.

The protruding portion of the free rotating ring may include an arcuate tab, and the first and second contact faces of the free rotating ring may be on opposite sides of the arcuate tab.

The arcuate tab of the free rotating ring may protrude radially inward.

The second rotation range may be defined by the opposite faces of the arcuate tab engaging the respective first and second contact faces of the spindle.

The spindle may include an arcuate tab, and the first and second contact faces of the spindle may be on opposite sides of the arcuate tab.

The arcuate tab of the spindle may protrude radially outward.

The camera assembly may include a protruding member, and the first rotation range may be defined by opposite sides of the protruding member engaging the respective first and second contact faces of the free rotating ring.

The protruding member may include a screw threaded into a wall of the bracket of the camera assembly, and the screw may protrude radially inward.

The free rotating ring may include a first arcuate tab, and the first and second contact faces of the free rotating ring may be on opposite sides of the first arcuate tab.

The first arcuate tab of the free rotating ring may protrude radially outward.

The protruding portion of the free rotating ring may include a second arcuate tab, and the second rotation range may be defined by opposite faces of the second arcuate tab engaging the respective first and second contact faces of the spindle.

The second arcuate tab may protrude radially inward.

The spindle may include an arcuate cutout, and opposite faces of the arcuate cutout may form the respective first and second contact faces of the spindle.

The surgical lighting system may further include a motor coupled to the bracket to rotate the bracket.

The motor may be mounted within the handle housing and may be fixed relative to the spindle.

The spindle may be a hollow cylindrical spindle that has an inner and outer circumference and the inner circumference may be continuous.

The camera may be configured to output an optical video signal.

According to another aspect of the invention, a method of rotating a camera of a surgical lighting system includes positioning a light head housing including a plurality of light emitting elements therein that are arranged to emit light downward to a region of interest; gripping a handle mounted to the light head housing and protruding downward from the light head housing, the handle including a handle housing having a sufficient size to be gripped by the human hand; and, rotating a camera assembly mounted within the handle housing, the camera assembly including a camera having a field of view that encompasses at least a portion of the region of interest; wherein rotating the camera assembly includes rotation greater than 360 degrees about a rotation axis from a first stop to a second stop and vice versa, wherein the first stop limits clockwise rotation of the camera about the rotation axis and the second stop limits counterclockwise rotation of the camera about the rotation axis.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

FIG. 7 shows a perspective top view of rotation components of the camera assembly of FIG. 5.

FIG. 8 shows an exploded perspective view of rotation components of the camera assembly of FIG. 5.

FIG. 12 shows a perspective top view of rotation components of a camera assembly according to another embodiment of the present application.

FIG. 13 shows an exploded perspective view of rotation components of the camera assembly of FIG. 12.

FIG. 14 shows a top plan view of rotation components of the camera assembly of FIG. 12, showing a mid-rotation position of the camera assembly.

FIG. 15 shows another top plan view of rotation components of the camera assembly of FIG. 12, showing a maximum clockwise position of the camera assembly after a clockwise rotational movement of the camera assembly that is greater than 360 degrees.

FIG. 16 shows another top plan view of rotation components of the camera assembly of FIG. 12, showing a maximum counterclockwise position of the camera assembly after a counterclockwise rotational movement of the camera assembly that is greater than 360 degrees.

DETAILED DESCRIPTION

Figure 1:
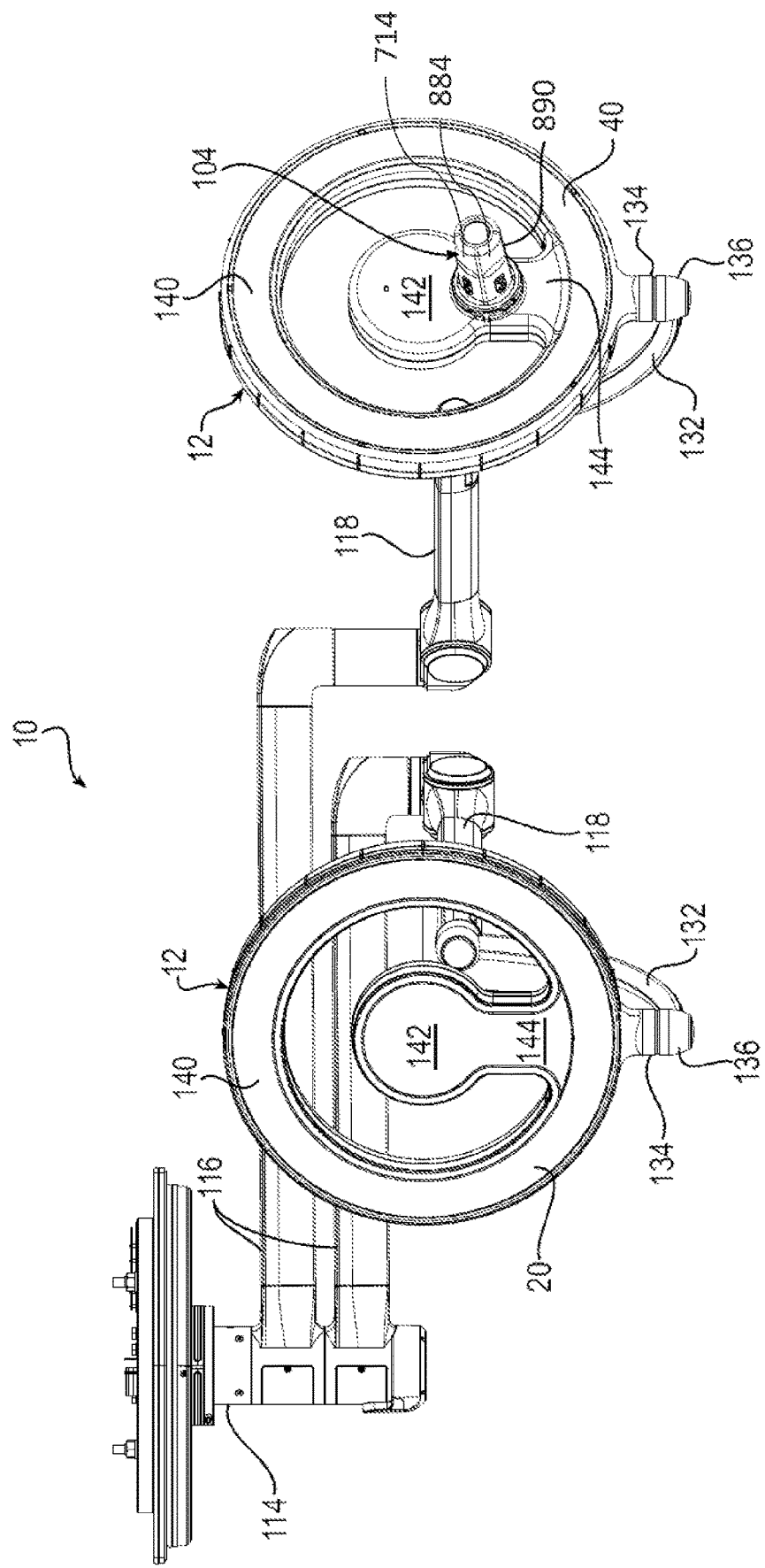
FIG. 1 is a side elevation view of an overall configuration of a medical device support system in accordance with an embodiment of the invention, showing a top of a left positioned light head and a bottom of a right positioned light head.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

The present application is directed to a rotatable camera assembly arranged in a surgical light head handle and a method of rotating a camera that may be suitable for use in various applications. An exemplary application includes surgical lights such as those used in operating rooms to provide increased light to a specific area of the room. For example, the rotatable camera assembly may be implemented in a handle housing mounted to a surgical light head housing that contains light emitting elements.

The surgical light system and method of rotating a camera assembly according to the present application includes a rotatable camera assembly arranged within a housing of a handle mounted to a light head housing. The camera assembly includes a camera having a field of view that encompasses at least a portion of a region of interest defined by light emitting elements supported in the light head housing. Rotation of the camera assembly relative to the handle housing is provided via an arrangement of rotatable components that is accommodated within the handle housing. The rotatable components include radially extending protrusions and/or tabs and/or cutouts that form different stops for limiting rotational movement of the camera assembly in both a clockwise rotational direction and in a counterclockwise rotation direction. The rotation stops are formed in a plane that is situated between the light head housing and the camera of the camera assembly.

The arrangement of the rotatable components provides a first rotation range and a second rotation range for the camera assembly that together enable a rotational movement of the camera assembly of greater than 360 degrees. The camera assembly is advantageously able to be mounted within the internal space of the handle housing. Thus, a handle for a surgical light that includes the rotatable camera assembly according to the present application is able to accommodate the rotatable camera assembly while still providing an ergonomic structure for improved use by an operator of the surgical light head.

Figure 2:
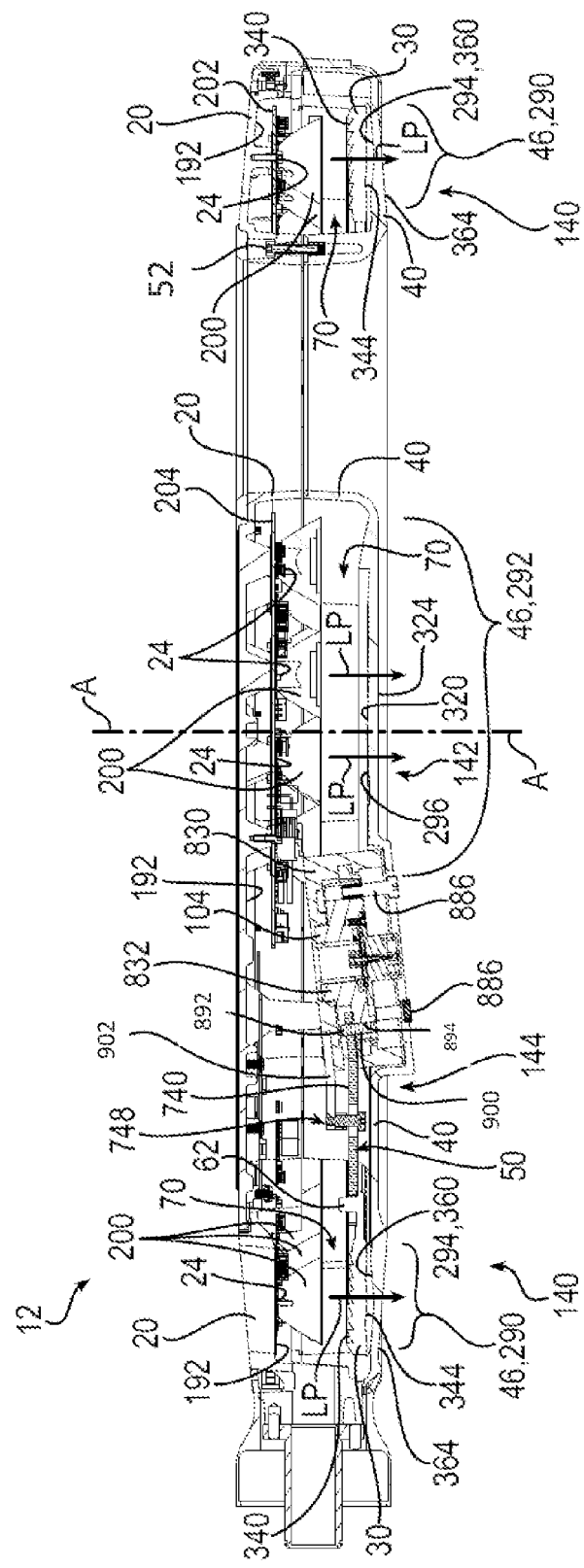
FIG. 2 is a side cross section view of a light head in accordance with an embodiment of the invention, showing a housing base, a housing cover, and internal components of the light head.

FIGS. 1 and 2 show a medical device support system 10 including two light heads 12 in accordance with an embodiment of the invention. Each light head 12 of the system 10 includes a housing base 20, a plurality of light emitting elements 24, an annular shape lens 30, a housing cover 40 including a housing lens 46, and a motion transfer member 50 which may include a lever, gear arrangement, or articulating assembly. The housing base 20 and the housing cover 40 are connected by fasteners 52. The annular shape lens 30 and the housing lens 46 are in a light emitting path LP of the plurality of light emitting elements 24.

Within a small structural envelope the motion transfer member 50 is configured to movably interact with a boss 62 of the annular shape lens 30 to rotate the annular shape lens 30 about a rotation axis A-A and within a cavity 70 of the housing cover 40. The motion transfer member 50 may be movably coupled to a driving source 104, such as a handle, of the light head 12 such that motion from the driving source 104 translates into rotation of the annular shape lens 30 about the rotation axis A-A; this also being provided within a low overall height structure advantageous for maneuverability of the light head 12 and a structure providing improved laminar flow conditions.

As shown in FIG. 1, the medical device support system 10 includes a central shaft or support column 114 that is suspended from the ceiling, and two generally horizontal extension arms 116 mounted to the shaft 114 for rotational movement about the shaft 114. The central shaft 114 could be mounted to a wall or stand rather than the ceiling. Two load balancing arms 118 are pivotably mounted to the distal ends of the respective extension arms 116. The distal ends of the load balancing arms 118 are configured with yoke assemblies 132 which, in turn, support the respective light heads 12 for multi-axis movement relative to the load balancing arms 118. Each light head 12 includes a bushing or other coupling member 134 that rotatably connects the light head 12 to the distal end of an arm 136 of a respective yoke assembly 132, as shown. The load balancing arms 118 and yoke assemblies 132 enable positioning of the light heads 12 to a proper orientation relative to for example a patient operating table and healthcare professionals in the operating room.

As shown in FIGS. 1 and 2, each light head 12 includes an annular shape outer portion 140, an inner round portion 142, and a radially protruding arm 144 that connects the annular shape outer portion 140 to the inner round portion 142. In the illustrative embodiment, the radially protruding arm 144 arranges the annular shape outer portion 140 and the inner round portion 142 in concentric relation to one another, and in concentric relation to the rotation axis A-A of the annular shape lens 30. The radially protruding arm 144 also houses the motion transfer member 50 and one or more components of the driving source 104, to be described in greater detail below, for driving the motion transfer member 50. A controller controls the light emitting elements 24 of the annular shape outer portion 140 and the inner round portion 142 to emit light to a surgical treatment site or other medical site below the light heads 12. It will be appreciated that the annular shape outer portion 140 and the inner round portion 142 need not be in concentric relation to one another and instead can be arranged by the protruding arm in eccentric relation to one another. It will further be appreciated that in an alternate embodiment the inner round portion 142 of the light head 12 may be omitted; and in such form, only the annular shape outer portion 140 emits light to the medical treatment site.

As shown in FIG. 2, an inside surface 192 of the housing base 20 supports the plurality of light emitting elements 24, which may be for example light emitting diodes (LEDs). In the illustrative embodiment, a plurality of collimators 200 are also mounted to the inside surface 192 of the housing base 20 and in the light emitting paths LP of the respective plurality of light emitting elements 24. The collimators 200 collect and direct, and/or collimate, the light into narrow beams. In one form, the collimators 200 may comprise total internal reflection (TIR) lenses. The light emitting elements 24 and collimators 200 may be grouped together in modules 202, 204 mounted to the inside surface 192 of the annular shape outer base 180 and one round module 204 mounted to the inside surface 192 of the inner round base 182.

The housing cover 40 also includes the housing lens 46, which in the illustrative embodiment includes an annular shape outer lens 290 and an inner round lens 292. The annular shape outer lens 290 forms a bottom wall 294 of the annular shape outer cover 240 and thus the bottom surface of the annular shape outer cavity 260. The inner round lens 292 forms a bottom wall 296 of the inner round cover 242 and thus the bottom surface of the inner round cavity 262. In an alternate form, the bottom wall of the annular shape outer cover 240 and/or the inner round cover 242 may be formed by a transparent non-lens material, i.e. a non-light bending material, and the annular shape outer lens 290 and/or the inner round lens 292 may be positioned for example above the transparent non-lens bottom walls and secured to surrounding structure of the housing cover 40.

FIG. 2 shows an axial arrangement of the light emitting elements 24, the collimators 200, the annular shape lens 30, and the housing lens 46, where axial refers to the direction of emission of light from the light heads 12, or downward in FIG. 2. The annular shape outer lens 290 and the inner round lens 292 are in the light emitting paths LP of the plurality of light emitting elements 24. The annular shape lens 30 is in the light emitting paths LP of the plurality of light emitting elements 24, positioned between the light emitting elements 24 and the annular shape outer lens 290. The collimators 200 are also arranged in the light emitting paths LP of the plurality of light emitting elements 24 in the annular shape outer portion 140 of the light head 12 positioned between the light emitting elements 24 and the annular shape lens 30, and in the inner round portion of the light head 12 positioned between the light emitting elements 24 and the inner round lens 292.

The annular shape lens 30 and the housing lens 46, and the collimators 200 if provided, can take on any form for spreading and/or bending the light emitted by the light emitting elements 24. As shown for example in FIG. 2, the inner round lens 292 of the housing lens 46 has a top face 320 formed as a stepped surface, for example a plurality of Fresnel wedges, that bends individual portions of the light beams, and a bottom face 324 formed as a generally planar surface. The annular shape lens 30 has a top face 340 formed as a stepped surface, for example a plurality of Fresnel wedges, that bends individual portions of the light beams, and a bottom face 344 formed as a wavy or curved surface. The annular shape outer lens 290 of the housing lens 46, meanwhile, has a top face 360 formed as a wavy or curved surface and a bottom face 364 formed as a generally planar wedge-shaped surface, where a generally planar wedge-shaped surface refers to a generally planar surface that is not perpendicular to the direction of travel of the light beam emitted by the light emitting elements 24 and collimators 200, for example.

Rotation of the annular shape lens 30 and its wavy surface 344 relative to the housing lens 46 and its wavy surface 360 results in beam spreading (focusing) of the light beam, while simultaneously bending (aiming) of the light beam is achieved by the wedge-shaped surfaces 340, 364 of the annular shape lens 30 and the housing lens 46. It will be appreciated that the annular shape lens 30 and the housing lens 46 need not be limited to the features and characteristics as shown and described herein and can include additional and/or alternate types of features and characteristics as necessary or desired to satisfy illumination requirements specific to an application. Further, it will be appreciated that the light head 12 may include additional lenses for bending and/or spreading of the light emitted by the light emitting elements 24.

The motion transfer member 50 movably interacts with the boss 62 of the annular shape lens 30 to rotate the annular shape lens 30 about the rotation axis A-A and within the annular shape outer cavity 260. In the illustrative embodiment, the annular shape lens 30 is circular and the rotation axis A-A constitutes the central axis of the circular annular shape lens 30. It will be appreciated that the annular shape lens 30 may have any curvilinear shape, whether circular as shown, elliptical, oval, among others. Moreover, the rotation axis A-A may be other than a central axis of the circular annular shape lens 30. For example, the rotation axis A-A may be offset from the central axis of the circular annular shape lens 30.

Also, in the illustrative embodiment, the rotation axis A-A constitutes the central axis of the light head 12 including the central axis of the housing base 20 and the central axis of the housing cover 40. The rotation axis A-A of the annular shape lens 30 need not be the same as (coincide with) the central axis of the light head 12 itself, or the same as (coincide with) the central axis of the housing base 20 and/or the housing cover 40. Thus, for example, the rotation axis A-A of the annular shape lens 30 may be offset from the central axis of the housing base 20 and/or housing cover 40, particularly where the light head 12 includes additional or alternate type control elements, handles, connection brackets, contours, among others.

The annular shape lens 30 is movable by interaction with the motion transfer member 50. In the movable interaction, the motion transfer member 50 moves the boss 62 and thus the annular shape lens 30 to, respectively, a neutral position, a position counterclockwise from the neutral position, and a position clockwise from the neutral position, from a perspective of looking from above the light head 12 downward into the cavity 70 of the light head 12. A driving source 104 and a motion transfer member 50 are used for imparting motion to the boss 62 of the annular shape lens 30. The driving source 104 includes a handle 714 including a rotatable camera assembly as will be described in further detail below.

Figure 3:
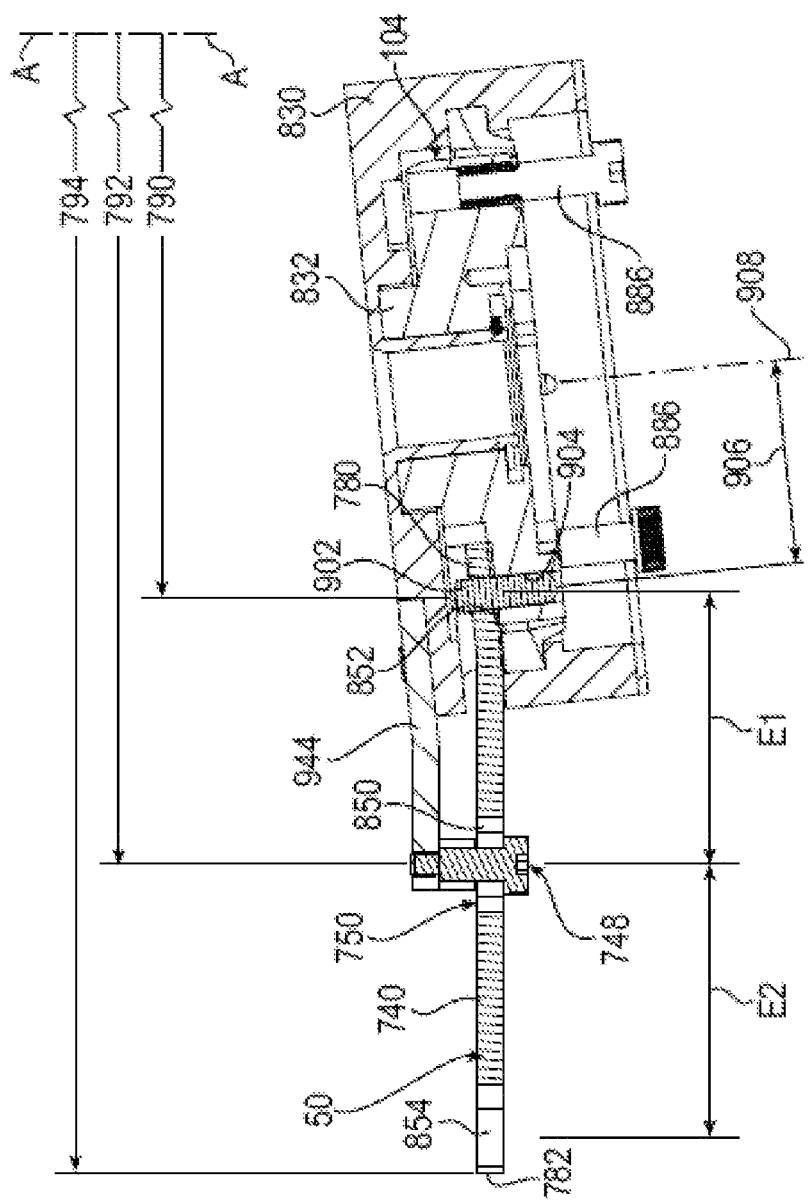
FIG. 3 is a side cross section view of a lever and a hub connectable with an upper portion of a handle.

Referring in addition to FIG. 3, in the illustrative embodiment, the motion transfer member 50 includes a lever 740. The lever 740 is movable relative to a fulcrum 748 of the light head 12 at a pivot slider portion 750 of the lever 740. As shown in FIG. 2, the entire lever 740 is configured to move relative to the fulcrum 748 within the depth of the cavity 70. The lever 740 includes a first end 780 and a second end 782 at opposite sides of the pivot slider portion 750 and thus at opposite sides of the fulcrum 748. The first end 780, the fulcrum 748, and the second end 782 are arranged at respective first, second, and third radial distances 790, 792, 794 from the rotation axis A-A, wherein the third radial distance 794 is greater than the second radial distance 792, and the second radial distance 792 is greater than the first radial distance 790. The arrangement of the lever 740 within the housing cover 40 contributes to a lower height light head 12 and facilitates a C-shape opening in the light head 12 structure that improves laminar flow in the vicinity of the light head 12.

The first end 780 is spaced a first distance E1 from the fulcrum 748. The second end 782 is spaced a second distance E2 from the fulcrum 748. The lever 740 is configured to transfer motion from the driving source 104 at the first end 780 of the lever 740 into rotational motion of the annular shape lens 30 about the rotation axis A-A and within the cavity 70 at the second end 782 of the lever 740 in response to movement of the lever 740, and more specifically the pivot slider portion 750 of the lever 740, relative to the fulcrum 748. The degree of motion from the driving source 104 and the resultant degree of rotation of the annular shape lens 30 is based on the ratio of the first distance E1 from the fulcrum 748 to the second distance E2 from the fulcrum 748. Accordingly, the location of the pivot slider portion 750 of the lever 740 provides the desired ratio of driving source 104 motion to annular shape lens 30 rotation. Thus, where the first and second distances E1, E2 are approximately equal and the driving source 104 imparts a driving motion on the first end 780 of the lever 740 about the fulcrum 748 of for example 5 degrees, the resultant degree of rotation of the annular shape lens 30 about the rotation axis A-A at the second end 782 of the lever 740 is about 5 degrees. Where the first distance E1 is greater than the second distance E2 and the driving source 104 imparts a driving motion on the first end 780 of the lever 740 about the fulcrum 748 of for example 5 degrees, the resultant degree of rotation of the annular shape lens 30 about the rotation axis A-A at the second end 782 of the lever 740 will be less than 5 degrees. Where the first distance E1 is less than the second distance E2 and the driving source 104 imparts a driving motion on the first end 780 of the lever 740 about the fulcrum 748 of for example 5 degrees, the resultant degree of rotation of the annular shape lens 30 about the rotation axis A-A at the second end 782 of the lever 740 will be greater than 5 degrees.

The driving source 104 includes the handle 714, as also shown in FIG. 1, which is rotatably mounted coaxially to a hub 830 of the light head 12. The first end 780 of the lever 740 is movably coupled to a bushing 832 of the handle 714 and the second end 782 of the lever 740 is movably coupled to the annular shape lens 30. The lever 740 is configured to transfer rotational motion of the handle 714 at the first end 780 of the lever 740 into rotational motion of the annular shape lens 30 at the second end 782 of the lever 740. Here, the degree of rotation of the handle 714 and the resultant degree of rotation of the annular shape lens 30 is based on the ratio of the first distance E1 from the fulcrum 748 to the second distance E2 from the fulcrum 748. Accordingly, the location of the pivot slider portion 750 of the lever 740 provides the desired ratio of handle 714 rotation to annular shape lens 30 rotation.

The lever 740 has an elongated shape. The pivot slider portion 750 of the lever 740 which is movably coupled to the fulcrum 748 of the light head 12 is located approximately at the center of the length of the lever 740 and defines therein an elongated central slot 850 that extends in the elongated direction of the lever 740. The first end 780 of the lever 740, i.e. the end of the lever 740 movably coupled to the handle 714, has a through hole 852. The second end 782 of the lever 740, i.e. the end of the lever 740 movably coupled to the annular shape lens 30, defines therein an elongated outward slot 854 that extends in the elongated direction of the lever 740 and opens outwardly in a direction away from the fulcrum 748.

The first end 780 of the lever 740 is coupled to the bushing 832 of the handle 714. The bushing 832 is rotatably mounted coaxially within the hub 830 which in turn is secured to the housing cover 40. A handle housing 890 of the handle 714 is connected to an upper "hat" portion which in turn is removably connectable to the bushing 832 by for example fasteners 886, described in greater detail below. Once hat portion and the handle housing 890 are connected to the bushing 832, the two rotate together as a single component, i.e. the handle 714 referred to herein. The handle housing 890 includes a grip portion 884 that can be grasped by the human hand, as will be described in greater detail below.

The first end 780 of the lever 740 is movably coupled to the bushing 832 of the handle 714 by a pin 892 secured in an opening 894 of the bushing 832 a radial distance 896 from, and parallel to, a central axis 898 of the hub 830. The pin 892 is rotatably mounted in the through hole 852 of the first end 780 of the lever 740. As will be appreciated, rotation of the handle 714 rotates the pin 892 and thus the first end 780 of the lever 740 along an arc shape path defined by the radial distance 896. The pin 892 rotates within the through hole 852 of the first end 780 of the lever 740 during such rotation. In an alternate form, the pin 892 may be secured in the through hole 852 of the lever 740 and rotatably mounted in the opening 894 of the bushing 832.

In the illustrative embodiment, the fulcrum 748 includes a round shape fastener 900 connected to a bracket 902 that is in turn secured to the hub 830 of the light head 12. The illustrated round shape fastener 900 is a shoulder bolt, as shown in FIG. 2. The diameter of the head 12 of the shoulder bolt is greater than the width of the elongated central slot 850 of the lever 740, while the diameter of the shank is slightly less than the width of the elongated central slot 850. In an alternate form, the fulcrum 748 and bracket 902 may constitute a single molded component made of for example a thermoplastic material. In an alternate form, the bracket 902 may be secured to the housing cover 40 or the housing base 20, or any combination of the hub 830, housing cover 40, and housing base 20. The central portion of the lever 740 is movably coupled to the shoulder bolt by the shank of the shoulder bolt being slidably movable within the elongated central slot 850 of the lever 740. As will be appreciated, owing to the first end 780 of the lever 740 moving along an arc shape path about the hub central axis 898 and the fulcrum 748 being fixed relative to the hub central axis 898, the central portion of the lever 740 via the elongated central slot 850 will both pivot about and slide along the shank of the shoulder bolt when the first end 780 of the lever 740 is moved by the handle 714.

The second end 782 of the lever 740 is movably coupled to the annular shape lens 30 by the afore described boss 62 of the annular shape lens 30. In the illustrative embodiment, the boss 62 has a round shape. The second end 782 of the lever 740 is movably coupled to the boss 62 by the boss 62 being slidably movable within the elongated outward slot 854 of the lever 740. As will be appreciated, owing to the first end 780 of the lever 740 moving along the arc shape path about the hub central axis 898 and the fulcrum 748 being fixed relative to the hub central axis 898, the second end 782 of the lever 740 via the elongated outward slot 854 will both pivot about and slide along the boss 62 when the first end 780 of the lever 740 is moved by the handle 714.

The rotation of the handle 714 moves the first end 780 of the lever 740 relative to the fulcrum 748, which translates into movement of the boss 62 at the second, or opposite, end of the lever 740 to rotate the annular shape lens 30 about the rotation axis A-A and within the cavity 70 of the housing cover 40. In the neutral position, the lever 740 protrudes substantially radially relative to the rotation axis A-A. The lever 740 is "pulled" or retracted slightly inward by the pin 892 coupled to the handle 714, causing the lever 740 to slide via the slots 850, 854 along the respective fulcrum 748 and boss 62. Further details of an exemplary surgical light system suitable for the present application are described in U.S. application Ser. No. 17/151,760 filed Jan. 19, 2021, and titled "Lighthead with Rotating Lens Assembly and Method of Operating Same," which is incorporated by reference for all purposes as if fully set forth herein.

Figure 5:
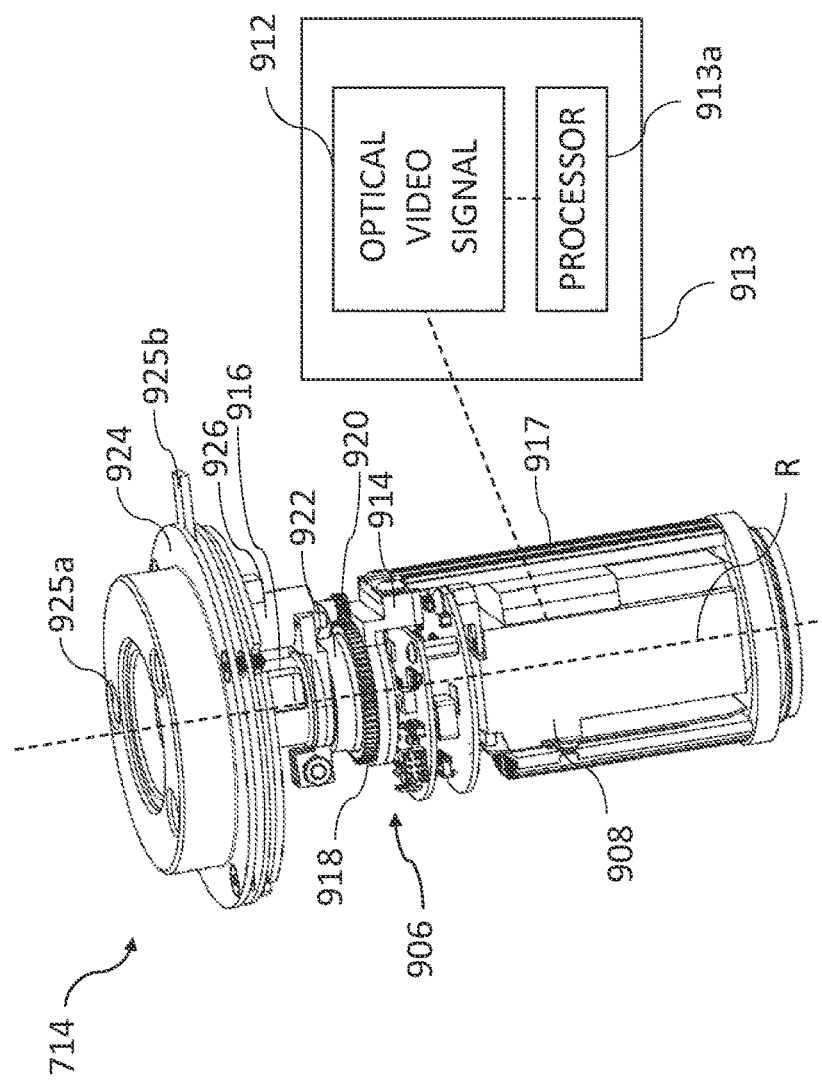
FIG. 5 shows a perspective side view of the handle of FIG. 4 with the handle housing removed, showing a rotatable camera assembly.
Figure 4:
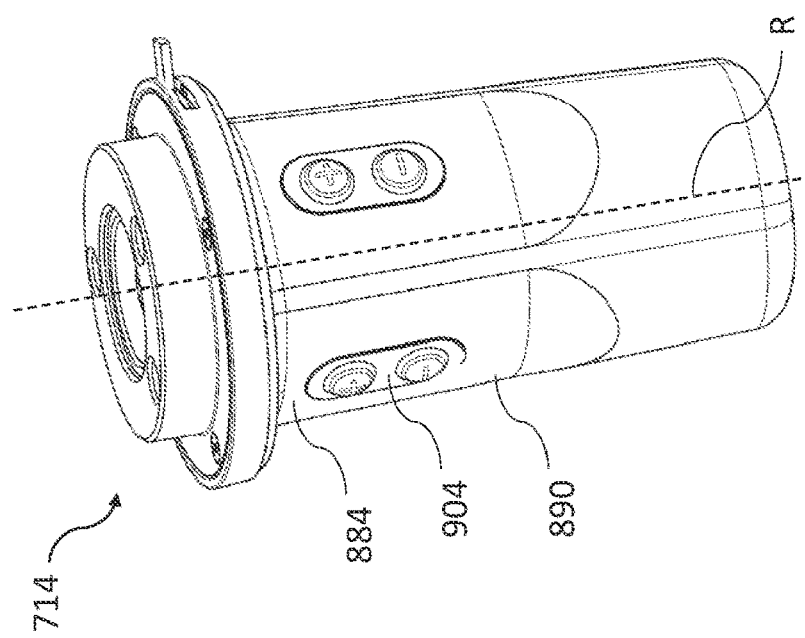
FIG. 4 shows a perspective side view of a handle having a handle housing including a grip portion.
Figure 6:
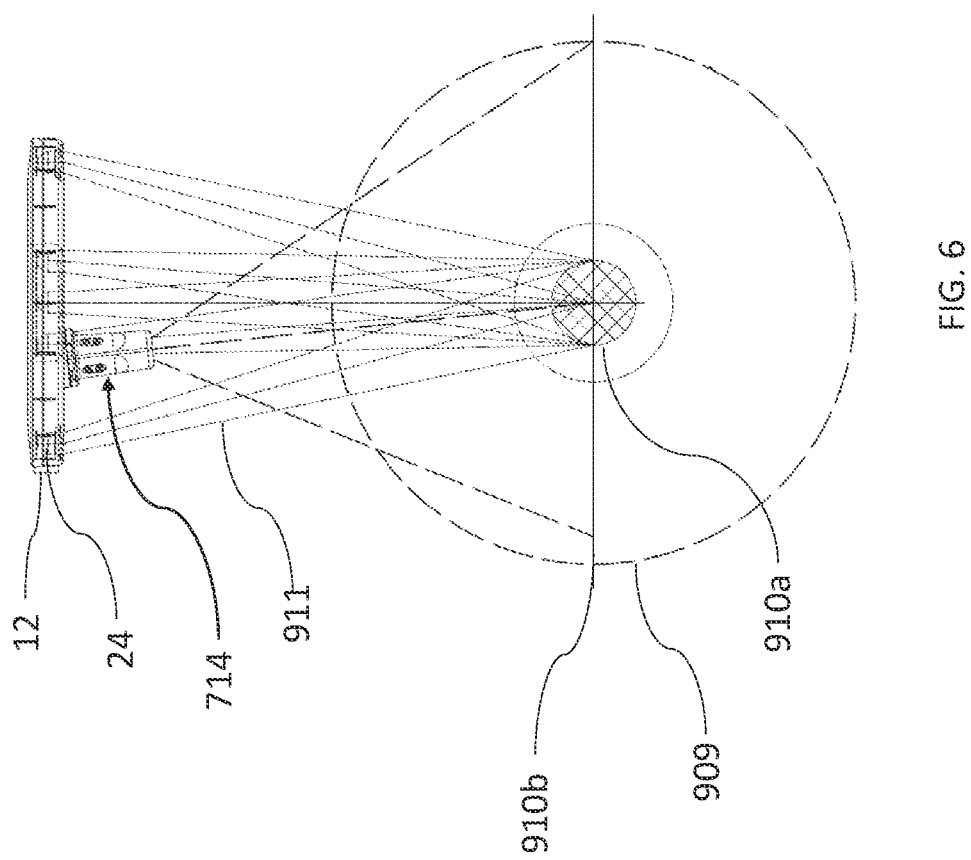
FIG. 6 shows a region of interest of the light head and a field of view of a camera in the camera assembly of FIG. 5.

FIGS. 4-6 show further details of the handle 714 according to an embodiment of the present application. FIG. 4 shows the handle 714 having the grip portion 884 of the handle housing 890 having buttons 904 that provide a user interface for the handle 714 for controlling attributes of the emitted light from the light head 12. In other embodiments, the handle 714 may be provided with buttons that interface with the drive motor 926 to rotate the camera assembly 906. The handle housing 890, including the grip portion 884 thereof, has a sufficient size to be gripped by a human hand meaning that the outermost diameter or perimeter of the handle housing 890 is selected to enable a human hand to be comfortably wrapped around the handle housing 890. The handle housing 890 may be cylindrical in shape and elongated along a rotation axis R. Other shapes may be suitable for the handle housing 890.

FIG. 5 shows the handle 714 with the handle housing 890 removed. The handle 714 includes a camera assembly 906 mounted within the handle housing 890 for rotation about the rotation axis R. As shown in FIG. 6, the camera assembly 906 has a camera 908 configured to provide a field of view 909 encompassing at least a portion of a region of interest 910a defined by the plurality of light emitting elements 24. The region of interest 910a may include a specific target, such as a patient on a surgical table 910b. A target may be defined as an area which the user intends to illuminate by aiming the light 911 produced by the surgical light. The region of interest 910a may be defined as the area that is illuminated by the light head 12 which is typically at a distance of one meter from the light head 12. "Target", "region of interest," "target region", and "target region of interest," etc. may be used with reference to the same area. The region of interest 910a may be formed by the light emitting elements 24 that emit light and lenses that aim, redirect, spread, converge, and or focus the light.

The camera 908 may include any suitable optical camera including a sensor and being configured to capture images within the region of interest 910a. For example, the camera 908 may include a complementary metal oxide semiconductor (CMOS) sensor. Other sensors may be suitable. In an exemplary embodiment, a CMOS sensor having approximately a 2,000,000 pixel resolution may be suitable. The camera 908 may have any suitable focal distance range, such as between 10 and 800 millimeters, and any suitable signal-to-noise ratio. The signal-to-noise ratio may exceed 50 decibels to provide clear images. In another exemplary embodiment, the camera 908 may include a surgical display having a resolution that is approximately 4096 by 2160, an aspect ratio of 1.9 to 1, and a viewing angle that is approximately 178 degrees. Further details of an exemplary means of integrating fiber optic capability into the light head handle for transmission of the optical video signal of the camera 908 from the handle housing 890 to the light head housing 20, 40 is described in U.S. Provisional Application No. 63/000,672 filed Mar. 27, 2020, titled "Light Head Having Camera Assembly Integrated in Handle and Surgical Lighting System Including Same," which is incorporated by reference for all purposes as if fully set forth herein. Many other cameras may be suitable.

Referring to FIG. 5, the camera 908 is configured to output an optical video signal 912 pertaining to images captured within the field of view 909 and the region of interest 910a. Of course, in other embodiments, the camera 908 may be configured to output an electrical video signal. The optical video signal 912 may be processed by a control system 913 of the medical device support system 10. For example, the optical video signal 912 may be received by a processor 913a in the control system 913. The control system 913 may be configured to output the optical video signal 912 as a viewable image to a user. The processor 913a may include any suitable microprocessor, control processing unit (CPU), control circuitry, or the like.

The camera assembly 906 is advantageously configured for rotation that is greater than 360 degrees about the rotation axis R in both a clockwise direction and in a counterclockwise direction. As will be described in detail below, first and second stops are provided to limit rotation of the camera assembly 906 and the camera assembly 906 is rotatable between the first and second stops. For example, first stop limits clockwise rotation of the camera assembly 906 about the rotation axis R and the second stop limits counterclockwise rotation of the camera assembly 906 about the rotation axis R. It should be recognized that, alternatively, the first stop may limit counterclockwise rotation and the second stop may limit clockwise rotation. The first and second stops are formed in a plane that is situated between the housing 20, 40 and the camera 908 which aids in enabling the camera assembly 906 to be mounted within the handle housing 890.

FIGS. 5 and 7-11 show a first embodiment of the camera assembly 906. The camera assembly 906 includes a bracket 914 and a spindle 916 that is fixed relative to the handle housing 890 of the handle 714. The bracket 914 is rotatably mounted to the spindle 916 and is fixed to an axially extending bracket 917. In the illustrative embodiment, the brackets 914, 917 together form a rotatable bracket 914, 917 having an inverted L shape, as shown in FIG. 5. It will be appreciated that the rotatable bracket 914, 917 may be of a unitary or monolithic construction rather than two fixedly connected portions 914, 917. The camera 908 is fixed to the axially extending bracket 917 such that the camera 908 is rotatable with rotation of the rotatable bracket 914, 917 about the spindle 916. A gear 918 is fixed to the bracket 914 and a pinion 920 is in meshing engagement with the gear 918 for driving the gear 918 and thus the rotatable bracket 914, 917.

A free rotating ring 922 is rotatable about a rotation axis R of the bracket 914. The free rotating ring 922 is movable relative to the bracket 914 and relative to the spindle 916. The free rotating ring 922, the bracket 914, and the spindle 916 are concentrically arranged relative to each other. The spindle 916 is fixed to a cover plate 924 or upper "hat" portion of the handle 714 that is engageable with the handle housing 890 and bushing 832, which, in turn, is rotatably mounted within the hub 830 of the light head 12, as shown in FIG. 3. It will be appreciated that any suitable mechanism may be used to connect the spindle 916, handle housing 890, and bushing 832 together, and any suitable coupling mechanism may be used to rotatably mount the bushing 832 relative to the hub 830 of the light head housing 20, 40. A bolt hole pattern 925a may be provided to receive fasteners 886. A radially extending tab 925b extending movably within a slot of the cover plate 924 enables attachment and removal of the handle 714 to and from the hub 830 of the light head 12, for example, by means of a latching assembly coupled to the tab 925 that is latchable to the hub 830. The radially extending tab 925b may be rotated to tighten the handle 714 relative to the hub 830 when the fasteners 886 are received in the bolt holes of the bolt hole pattern 925a. As will be appreciated, any suitable means may be employed to rotatably mount the handle 714 to the hub 830 of the light head 12.

A drive motor 926 is also accommodated in the handle housing 890 and the pinion 920 is mounted on the axis of the drive motor 926 such that the pinion 920 is rotatable by the drive motor 926. The spindle 916 and the drive motor 926 are fixedly mounted to the handle housing 890 such that the rotatable bracket 914, 917 and the free rotating ring 922 are movable relative to the fixed components.

FIGS. 7 and 8 show further details of the camera assembly 906. The bracket 914 may form a lowermost portion of the camera assembly 906 relative to the location at which the handle 714 is mounted to the hub 830 of the light head 12. The bracket 914 includes a cylindrical base 928 and a stepped portion 930 that is stepped downwardly relative to the cylindrical base 928. The stepped portion 930 is secured to the axially extending bracket 917 of the camera assembly 906, as shown in FIG. 5. The cylindrical base 928 and the stepped portion 930 may be formed as an integral and continuous part of unitary or monolithic construction. In the illustrative embodiment, the cylindrical base 928 and the stepped portion 930 share the same upper surface to which the gear 918 is fixed. The gear 918 is arranged axially above the cylindrical base 928 such that teeth 931 of the gear 918 extend normal to the upper surface of the cylindrical base 928.

The bracket 914 further includes a cylindrical wall 935 having an outer diameter that is less than the outer diameter of the gear 918 and extends axially upwardly from the gear 918. A cylindrical wall 933 having an arcuate cutout 932 extends axially upwardly from the cylindrical wall 935 and has a noncontinuous outer diameter that is less than the outer diameter of the cylindrical wall 935. The cylindrical wall 935 is continuous along the outer diameter whereas the cylindrical wall 933 defines an open space, i.e. arcuate cutout 932, having opposite faces 942, 944. The cylindrical wall 933 and its arcuate cutout 932 may have an axial height that is greater than the height of each of the cylindrical wall 933, the cylindrical base 928, and the gear 918. The bracket 914 may be formed as an integral component that is axially stepped radially inward in an upward direction from the cylindrical base 928 to the gear 918 to the cylindrical wall 935 to the cylindrical wall 933 and its arcuate cutout 932.

The free rotating ring 922 is cylindrical in shape and axially slidably engages against the upper surface of the cylindrical wall 935 of the bracket 914. The outer diameter of the cylindrical wall 933 is slightly less than the inner diameter of the free rotating ring 922 such that the cylindrical wall 933 and its arcuate cutout 932 are circumferentially surrounded by the free rotating ring 922. In this way, the outer diameter of the cylindrical wall 933 guides rotational movement of the free rotating ring 922, more specifically the inner diameter thereof, about the rotation axis R, where the cylindrical wall 933 and the free rotating ring 922 are in the same plane, i.e. the plane situated between the light head housing 20, 40 and the camera 908. The outer diameter of the free rotating ring 922 is a continuous peripheral surface 934 whereas the inner diameter includes a protruding portion 936 that extends radially inwardly and normal relative to the inner diameter of the free rotating ring 922. The illustrative protruding portion 936 is formed as an arcuate tab having opposing contact faces 938, 940 that extend radially inwardly. Each contact face 938, 940 is continuous with the inner diameter of the free rotating ring 932 via an arcuate surface. The protruding portion 936 may be integrally formed as part of the free rotating ring 922 such that the free rotating ring 922 is a monolithic structure. Alternatively, the protruding portion 936 may be connected to the inner diameter of the free rotating ring 922.

The opposite faces 942, 944 of the arcuate cutout 932 in the cylindrical wall 933 of the bracket 914 are engageable with the contact faces 938, 940 of the protruding portion 936 of the free rotating ring 922, respectively. A fixed distance arcuate space is defined between the opposite faces 942, 944 of the arcuate cutout 932 such that the protruding portion 936 has angular movement within and circumferentially along the arcuate cutout 932 during rotation of the camera assembly 906 about the rotation axis R. The opposite faces 942, 944 of the arcuate cutout 932 extend axially along the rotation axis R and substantially parallel with and in the same plane as the contact faces 938, 940 of the protruding portion 936 of the free rotating ring 922 such that the opposite faces 942, 944 and the contact faces 938, 940 matingly engage each other.

The contact faces 938, 940 of the protruding portion 936 of the free rotating ring 922 are also configured for engagement with a radially protruding portion 946 of the spindle 916. The illustrative protruding portion 946 is in the form of an integral arcuate tab extending radially outwardly from a peripheral surface 948 of the spindle 916. The spindle 916 may be formed as a monolithic component such that the protruding portion 946 is continuously formed as part of the spindle 916. The spindle 916 is a hollow cylindrical structure having an inner and outer circumference with the inner circumference being continuous and the outer circumference defining the peripheral surface 948. The spindle 916 has an axial length that is greater than the axial length of the free rotating ring 922. The diameter of the peripheral surface 948 is radially inwardly spaced from the diameter of the free rotating ring 922 to form an annular gap within which projects the cylindrical wall 933 and its arcuate cutout 932. As such, the spindle 916 is surrounded by the bracket 914 and the free rotating ring 922, and the cylindrical wall 933 and its arcuate cutout 932 are radially interposed between the spindle 916 and the free rotating ring 922.

The protruding portion 946 of the spindle 916 has opposing contact faces 950, 952 that are engageable with the contact faces 938, 940 of the protruding portion 936 of the free rotating ring 922, respectively. The contact faces 950, 952 extend axially and substantially parallel with the contact faces 938, 940 of the protruding portion 936 of the free rotating ring 922 such that the contact faces 938, 940, 950, 952 are configured for matingly engaging each other. A radial length of the protruding portion 936 of the free rotating ring 922 is greater than the radial length of the opposite faces 942, 944 of the arcuate cutout 932 and the contact faces 950, 952 of the spindle 916 such that one of the contact faces 938, 940 of the protruding portion 936 may simultaneously engage the corresponding one of the opposite faces 942, 944 of the arcuate cutout 932 and the corresponding one of the contact faces 950, 952 of the spindle 916. More specifically, the radial distance of the radially innermost portion of the protruding portion 936 of the free rotating ring 922 from the rotation axis R is less than the radial distance of the inner diameter of the cylindrical wall 933 from the rotation axis R. Further, the radial distance of the radially outermost portion of the protruding portion 946 of the spindle 916 from the rotation axis R is greater than the radial distance of the radially innermost portion of the protruding portion 936 of the free rotating ring 922 from the rotation axis R. In this way, the protruding portion 936 of the free rotating ring 922 is engageable not only with the opposite faces 942, 944 of the arcuate cutout 932 at a first radial distance from the rotation axis R but also with the opposite contact faces 950, 952 of the protruding portion 946 of the spindle 916 at a second radial distance from the rotation axis R, where the first radial distance is greater than the second radial distance. The camera assembly 906 further includes a snap ring 954 that is provided for axial engagement between the spindle 916 and the rotatable bracket 914, 917 that maintains the axial position of the rotatable bracket 914, 917 and also enables rotation therebetween.

The camera assembly 906 having rotation that is greater than 360 degrees is a compound of a first rotation range and a second rotation range. The sizes of the arcuate cutout 932 and the arcuate span of the protruding portion 936 of the free rotating ring 922 and the protruding portion 946 of the spindle 916 enable the angle of bracket rotation about the spindle 916. The protruding portion 936 has an arcuate span that enables a first contact face 938 of the protruding portion 936 to first engage a first face 942 of the arcuate cutout 932 and then subsequently contact face 940 of protruding portion 936 engages a first contact face 952 of the protruding portion 946 of the spindle 916, such as during a clockwise rotation of the camera assembly 906. The arcuate span of the protruding portion 936 also enables a second contact face 940 of the protruding portion 936 to first engage a second face 944 of the arcuate cutout 932 and subsequently contact face 938 of the protruding portion 936 engages a second contact face 950 of the protruding portion 946 of the spindle 916, such as during a counterclockwise rotation of the camera assembly 906.

The first rotation range for the camera assembly 906 may be defined by travel of the bracket 914 until one of the faces 942, 944 of the arcuate cutout 932 of the bracket 914 engages the corresponding one of the first and second contact faces 938, 940 of the protruding portion 936 of the free rotating ring 922. When the drive motor 926 rotates the pinion 920, the bracket 914 is driven in rotation such that the cylindrical wall 933 and its arcuate cutout 932 is rotated in the first rotation range. When the arcuate cutout 932 is rotated, the corresponding one of the faces 942, 944 of the arcuate cutout 932 engages the corresponding contact face 938, 940 of the protruding portion 936 of the free rotating ring 922 to carry the free rotating ring 922 in rotation with the bracket 914. The second rotation range is defined by the rotation of the bracket 914 and the free rotating ring 922 until the protruding portion 936 of the free rotating ring 922 engages the corresponding one of the first and second contact faces 950, 952 of the protruding portion 946 of the spindle 916. The free rotating ring 922 is carried by rotation of the bracket 914 until the protruding portion 936 of the free rotating ring 922 engages against the protruding portion 946 of the spindle 916.

Accordingly, the first stop for limiting rotational movement of the camera assembly 906, via the coupling between the camera assembly 906 and the spindle 916 shown in FIG. 5, is defined by the first contact face 938 of the free rotating ring 922 engaging the first face 942 of the arcuate cutout 932, and the second contact face 940 of the free rotating ring 922 engaging the second contact face 952 of the spindle 916. Thus, the first stop is configured to limit rotational movement in the clockwise direction. The second stop for the camera assembly 906 is defined by the second contact face 940 of the free rotating ring 922 engaging the second face 944 of the arcuate cutout 932 and the first contact face 938 of the free rotating ring 922 engaging the first contact face 950 of the spindle 916. Thus, the second stop is configured to limit rotational movement in the counterclockwise direction. The arrangement of the components is substantially symmetrical such that the rotation is similarly limited in both rotational directions.

Figure 11:
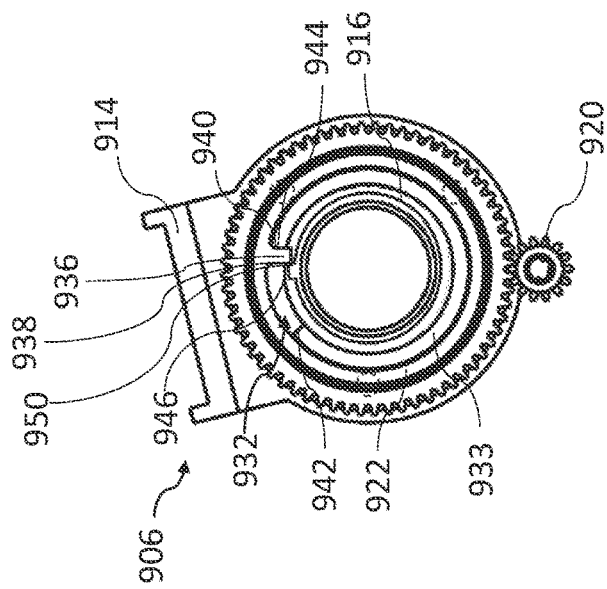
FIG. 11 shows another top plan view of rotation components of the camera assembly of FIG. 5, showing a maximum counterclockwise position of the camera assembly after a counterclockwise rotational movement of the camera assembly that is greater than 360 degrees.
Figure 10:
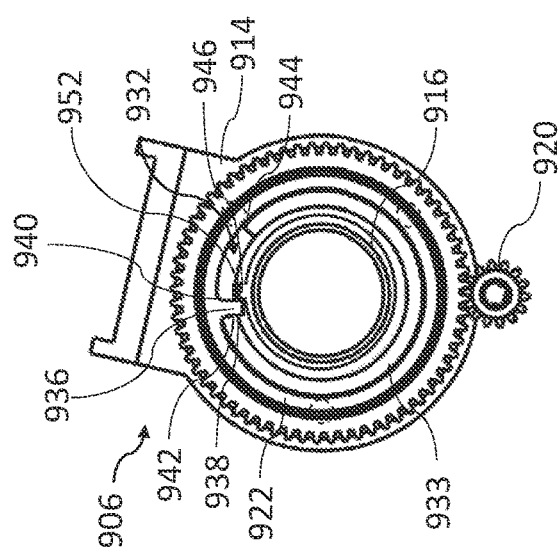
FIG. 10 shows another top plan view of rotation components of the camera assembly of FIG. 5, showing a maximum clockwise position of rotation components of the camera assembly after a clockwise rotational movement of the camera assembly that is greater than 360 degrees.
Figure 9:
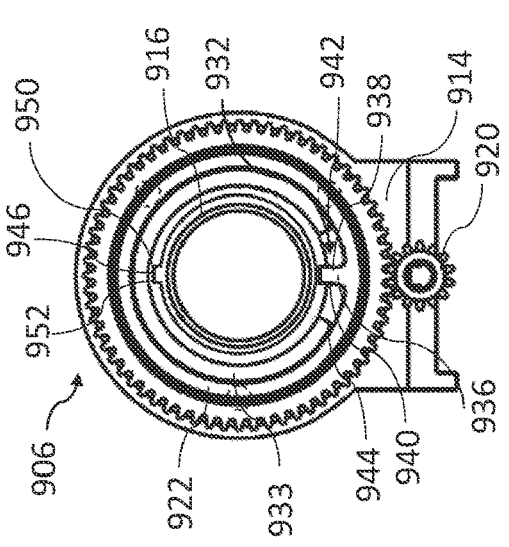
FIG. 9 shows a top plan view of rotation components of the camera assembly of FIG. 5, showing a mid-rotation position of the camera assembly.

FIGS. 9-11 show the different rotation positions of the camera assembly 906. FIG. 9 shows a mid-rotation position of the camera assembly 906 in which the bracket 914 is rotated by the pinion 920 such that the protruding portion 936 of the free rotating ring 922 is arranged between the opposite faces 942, 944 of the arcuate cutout 932. When the camera assembly 906 is in the mid-rotation position, the protruding portion 936 of the free rotating ring 922 is disengaged from the opposite faces 942, 944 of the arcuate cutout 932. The rotatable bracket 914, 917 is ready to rotate about the spindle 916 and thus the rotation axis R in either a clockwise or counterclockwise direction. The protruding portion 946 of the spindle 916 is disengaged from the protruding portion 936 of the free rotating ring 922 and from the opposite faces 942, 944 of the arcuate cutout 932. It will be appreciated that in the mid-rotation position the free rotating ring 922 may be positioned such that the protruding portion 936 thereof is centrally located within the arcuate span of the arcuate cutout 932, as shown in FIG. 9, or such that the protruding portion 936 abuts one of the opposite faces 942, 944 of the arcuate cutout 932, it being understood that the free rotating ring 922 is able to rotate substantially freely relative to the spindle 916 and the cylindrical wall 933 (subject to frictional resistance relative to the upper surface of the cylindrical wall 935).

FIG. 10 shows a maximum clockwise position in which the camera assembly 906 is rotated in the clockwise position until the first stop limits clockwise rotation of the camera about the rotation axis R. The rotatable bracket 914, 917 is rotated in the clockwise direction such that the arcuate cutout 932 is rotated and the first face 942 of the arcuate cutout 932 engages the first contact face 938 of the protruding portion 936 of the free rotating ring 922. The rotatable bracket 914, 917 carries the free rotating ring 922 in the clockwise direction until the opposing contact face 940 of the protruding portion 936 of the free rotating ring 922 engages the second contact face 952 of the protruding portion 946 of the spindle 916.

FIG. 11 shows a maximum counterclockwise position in which the camera assembly 906 is rotated in the counterclockwise position until the second stop limits counterclockwise rotation of the camera about the rotation axis R. The rotatable bracket 914, 917 is rotated in the counterclockwise direction such that the arcuate cutout 932 is rotated and the second face 944 of the arcuate cutout 932 engages the second contact face 940 of the protruding portion 936 of the free rotating ring 922 that opposes the first contact face 938. The free rotating ring 922 is then carried by the rotation of the rotatable bracket 914, 917 in the counterclockwise direction until the first contact face 938 of the protruding portion 936 of the free rotating ring 922 engages the first contact face 950 of the protruding portion 946 of the spindle 916.

The rotation of the rotatable bracket 914, 917, and thus the camera 908, from the maximum clockwise position of FIG. 10 to the maximum counterclockwise position of FIG. 11 shows that the camera 908 is rotatable greater than 360 degrees about the rotation axis R. Starting from FIG. 10, the first rotation range is equal to the arcuate span of the arcuate cutout 932 less the arcuate span of the protruding portion 936 of the free rotating ring 922. For an arcuate cutout 932 having an arcuate span of, for example, 55 degrees, and a protruding portion 936 having an arcuate span of, for example, 10 degrees, the first rotation range is about 45 degrees. The second rotation range is equal to 360 degrees less the arcuate span of the protruding portion 936 of the free rotating ring 922 less the arcuate span of the protruding portion 946 of the spindle 916. For a protruding portion 936 having an arcuate span of, for example, 10 degrees, and a protruding portion 946 having an arcuate span of, for example, 10 degrees, the second rotation range is about 340 degrees. Thus, the total rotation range of the camera 908 from the maximum clockwise position of FIG. 10 to the maximum counterclockwise position of FIG. 11 is about 340 degrees plus 45 degrees, or about 385 degrees. It will be appreciated that the arcuate spans of the arcuate cutout 932, protruding portion 936, and the protruding portion 946 may be altered to realize other first, second, and total rotation ranges.

Referring now to FIGS. 12 and 13, a camera assembly 906' according to another embodiment of the present application is shown in which the rotation of the camera assembly 906' that is greater than 360 degrees is enabled by a free rotating ring including two arcuate tabs and a bracket including a radially inwardly protruding screw. The camera assembly 906' has a rotation axis R and includes a bracket 914' that is rotatably mounted to a spindle 916' and is fixed to an axially extending bracket 917, as shown in FIG. 5. The bracket 914' and the axially extending bracket 917 together form a rotatable bracket as previous described. The camera assembly 906' may also include the camera 908 having the field of view 909 shown in FIGS. 5 and 6. The bracket 914' is rotatably mounted to the spindle 916' and a gear 918' is fixed to the bracket 914' for meshing engagement with a pinion 920' that is rotatable by a motor fixed to the handle housing, as shown in FIGS. 4 and 5. A free rotating ring 922' is rotatable about a rotation axis of the bracket 914' and is movable relative to the bracket 914' and relative to the spindle 916'.

The bracket 914' further includes a circumferential wall 932' that extends axially upwardly from a cylindrical base 928' of the bracket 914' and past the gear 918'. The circumferential wall 932' may have an axial length that is greater than the axial length of the cylindrical base 928' and the gear 918', and an outer diameter that is less than the outer diameter of the gear 918' and the cylindrical base 928'. A cylindrical sleeve 933' that is a separate component relative to the bracket 914' may be configured to be received within the inner diameter of the bracket 914' such that the free rotating ring 922' is axially supported against the cylindrical sleeve 933' such that the circumferential wall 932' radially surrounds the free rotating ring 922'. In other exemplary embodiments, the supporting surface for the free rotating ring 922' provided by the cylindrical sleeve 933' may be formed integrally with the bracket 914' as a unitary or monolithic structure.

The free rotating ring 922' is cylindrical in shape and may have a peripheral wall 934' that is continuous such that the free rotating ring 922' is closed. A first protruding portion 936a may be in the form of a first arcuate tab that extends radially inwardly from the peripheral wall 934' and a second protruding portion 936b may be in the form of a second arcuate tab that extends radially outwardly from the peripheral wall 934'. The protruding portions 936a, 936b may be formed integrally with the free rotating ring 922' such that the free rotating ring 922' is a monolithic component. The first protruding portion 936a is rotatable in an arcuate cutout 946' formed in the spindle 916' such that opposing faces 950', 952' of the cutout 946' limit rotation of the first protruding portion 936a. A screw 956 is threaded into a fastener hole 958 formed on the circumferential wall 932' of the bracket 914'. The screw 956 protrudes radially inwardly toward the free rotating ring 922'. The camera assembly 906' further includes a snap ring 954' for engagement between the spindle 916' and the bracket 914' that enables rotational movement of the bracket 914'. Other protruding structures other than a screw may be suitable. For example, a pin or post may be used. Using the screw 956 may be advantageous in enabling easier assembly and repeatable installation of the camera assembly 906'.

The rotation of the camera assembly 906' that is greater than 360 degrees is a compound of a first rotation range and a second rotation range. The size of the arcuate cutout 946' of the spindle 916' and the widths of the protruding portions 936a, 936b of the free rotating ring 922' enable the angle of bracket rotation about the spindle 916'. The first protruding portion 936a has opposing contact faces 938a, 940a that are engageable with opposing faces 950', 952' of the arcuate cutout 946' of the spindle 916', respectively. The second protruding portion 936b has opposing contact faces 938b, 940b that are engageable with opposing sides of the screw 956.

The first rotation range for the camera assembly 906' may be defined by rotation of the bracket 914' such that a corresponding side of the screw 956 secured in the circumferential wall 932' of the bracket 914' engages one of the opposing contact faces 938b, 940b of the second protruding portion 936b of the free rotating ring 922'. The bracket 914' carries the free rotating ring 922' in rotation via engagement with the screw 956. The second rotation range may be defined by movement of the first protruding portion 936a within the arcuate cutout 946' of the spindle 916' until movement of the first protruding portion 936a and thus the camera assembly 906' is limited via engagement of either the first contact face 938a of the first protruding portion 936a with the first opposing face 950' of the arcuate cutout 946' or the second contact face 940a of the first protruding portion 936a with the second opposing face 952' of the arcuate cutout 946'.

The first stop for the camera assembly 906' is defined by the screw 956 engaging the first contact face 938b of the second protruding portion 936b of the free rotating ring 922' and the first contact face 938a of the first protruding portion 936a engaging the first opposing face 950' of the arcuate cutout 946' of the spindle 916'. The first stop limits rotation of the camera assembly 906' in the clockwise direction. The second stop for the camera assembly 906' is defined by the screw 956 engaging the second contact face 940b of the second protruding portion 936b and the second contact face 940a of the first protruding portion 936a engaging the second opposing face 952' of the cutout 946' of the spindle 916'. The second stop limits rotation of the camera assembly 906' in the counterclockwise direction.

FIGS. 14-16 show different rotational positions of the camera assembly 906'. FIG. 14 shows a mid-rotation position of the camera assembly 906' in which the first protruding portion 936a of the free rotating ring 922' is arranged between the opposing faces 950', 952' of the spindle 916' and the screw 956 is arranged distally opposite to the second protruding portion 936b of the free rotating ring 922'. When the camera assembly 906' is in the mid-rotation position, the first protruding portion 936a is disengaged from the opposing faces 950', 952' of the spindle 916' and the second protruding portion 936b is disengaged from the screw 956. The bracket 914' is ready to rotate about the spindle 916' and thus the rotation axis R in either a clockwise or counterclockwise direction.

FIG. 15 shows a maximum clockwise position in which the camera assembly 906' is rotated in the clockwise position until the first stop limits clockwise rotation of the camera. The bracket 914' is rotated by rotation of the pinion 920' in the clockwise direction such that the circumferential wall 932' is rotated and the screw 956 supported in the circumferential wall 932' is rotated therewith. A first edge 960a of the screw engages the first contact face 938b of the second protruding portion 936b of the free rotating ring 922'. The free rotating ring 922' is then carried in the clockwise direction such that the first protruding portion 936a of the free rotating ring 922 is also rotated until the first contact face 938a engages the first contact face 950' of the arcuate cutout of the spindle 916'.

FIG. 16 shows a maximum counterclockwise position in which the camera assembly 906' is rotated in the counterclockwise position until the second stop limits the counterclockwise of the camera. The bracket 914' is rotated in the counterclockwise direction such that the circumferential wall 932' is rotated and a second edge 960b of the screw 956 that opposes the first edge 960a engages the second contact face 940b of the second protruding portion 936b of the free rotating ring 922'. The free rotating ring 922' is then carried in the counterclockwise direction until the second contact face 940a of the first protruding portion 936a of the free rotating ring 922' engages the second contact face 952' of the arcuate cutout of the spindle 916'.

Figure 17:
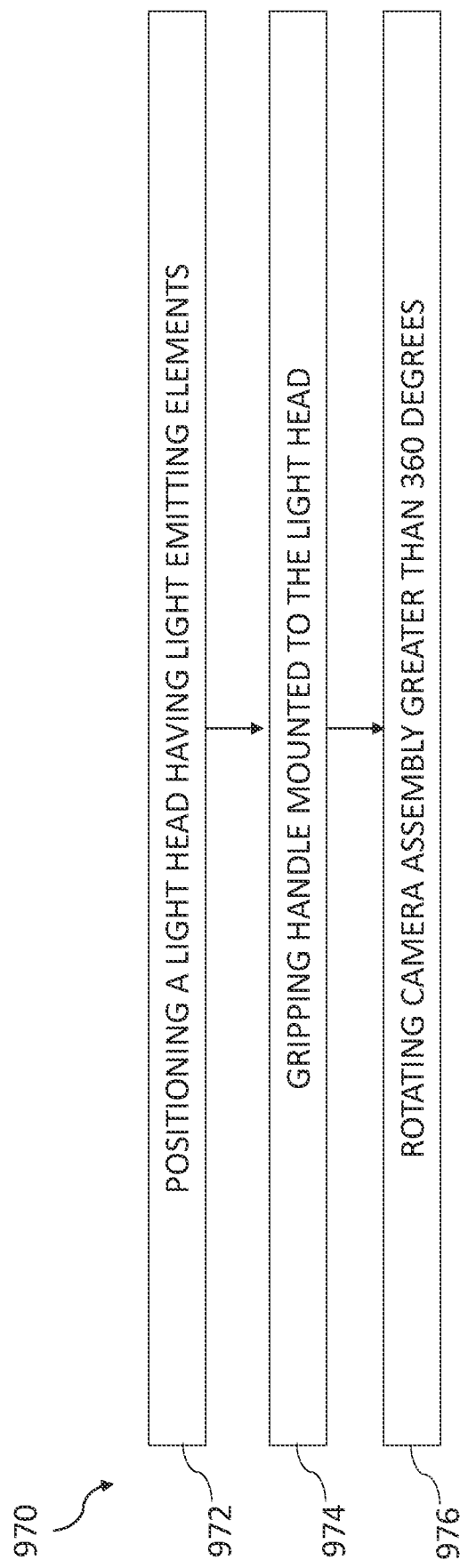
FIG. 17 is a flowchart showing a method of rotating a camera of a surgical lighting system, such as the camera assembly of FIG. 7 or FIG. 12.

FIG. 17 shows a flowchart 970 of a method of rotating a camera of a surgical lighting system such as the afore described light head 12 including the camera assembly 906, 906'. At step 972, a light head 12 is provided that includes a plurality of light emitting elements 24 that are arranged to emit light downward to a region of interest 910a, as shown in FIG. 6. At step 974, a handle 714 that is mounted to the light head 12 is gripped by a human hand. The handle 714 protrudes downward from the light head 12 and includes a handle housing 890 with a grip portion 884, as shown in FIG. 4. At step 976, a camera assembly 906, 906' is rotated within the handle housing 890. The camera assembly 906, 906' includes a camera having a field of view 909 that encompasses at least a portion of the region of interest 910a, as shown in FIG. 6. Rotating the camera assembly 906, 906' includes rotation greater than 360 degrees about a rotation axis R from a first stop to a second stop and vice versa, with the first stop limiting clockwise rotation of the camera about the rotation axis R, as shown in FIGS. 10 and 15, and the second stop limits counterclockwise rotation of the camera about the rotation axis R, as shown in FIGS. 11 and 16.

The surgical light head and method having any combination of the features described herein is advantageous in that the camera is able to be rotated greater than 360 degrees and accommodated in a limited amount of space within the handle housing. The limited amount of space is due to the handle housing being ergonomic and enabling the hand of an operator to be wrapped around the handle housing. The containment of the camera assembly within the handle housing is advantageous as compared with conventional camera rotation configurations which use larger protrusions that may snag cables. The camera assembly described herein uses integrally formed tabs that limit rotation in both the clockwise and counterclockwise direction while also enabling accommodation in a smaller amount of space. Still another advantage of the camera assembly is that the camera assembly may be more easily and repeatably installed.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A surgical lighting system, comprising:
   a light head housing including a plurality of light emitting elements therein that are arranged to emit light downward to a region of interest;
   a handle mounted to the light head housing and protruding downward from the light head housing, the handle including a handle housing having a sufficient size to be gripped by a human hand; and,
   a camera assembly mounted within the handle housing, the camera assembly including a camera having a field of view that encompasses at least a portion of the region of interest;
   wherein the camera assembly is mounted within the handle housing for rotation within the handle housing greater than 360 degrees about a rotation axis from a first stop to a second stop and vice versa, wherein the first stop limits clockwise rotation of the camera about the rotation axis and the second stop limits counterclockwise rotation of the camera about the rotation axis.

2. The surgical lighting system of claim 1, wherein the first and second stops lie in a plane situated between the light head housing and the camera.

3. The surgical lighting system of claim 1, wherein the camera assembly includes a bracket that is rotatably mounted to a spindle fixed relative to the handle housing.

4. The surgical lighting system of claim 3, further comprising a free rotating ring that is rotatable about the rotation axis and is movable relative to the bracket and movable relative to the spindle.

5. The surgical lighting system of claim 4, wherein the rotation greater than 360 degrees is a compound of a first rotation range and a second rotation range, the first rotation range defined by the camera assembly engaging first and second contact faces of the free rotating ring, the second rotation range defined by a protruding portion of the free rotating ring engaging first and second contact faces of the spindle.

6. The surgical lighting system of claim 5, wherein the first stop includes the camera assembly engaging the first contact face of the free rotating ring, and the protruding portion of the free rotating ring engaging the first contact face of the spindle.

7. The surgical lighting system of claim 5, wherein the second stop includes the camera assembly engaging the second contact face of the free rotating ring, and the protruding portion of the free rotating ring engaging the second contact face of the spindle.

8. The surgical lighting system of claim 5, wherein the bracket of the camera assembly includes an arcuate cutout, and the first rotation range is defined by opposite faces of the arcuate cutout engaging the respective first and second contact faces of the free rotating ring.

9. The surgical lighting system of claim 5, wherein the protruding portion of the free rotating ring includes an arcuate tab, and the first and second contact faces of the free rotating ring are on opposite sides of the arcuate tab.

10. The surgical lighting system of claim 9, wherein the arcuate tab of the free rotating ring protrudes radially inward.

11. The surgical lighting system of claim 9, wherein the second rotation range is defined by the opposite faces of the arcuate tab engaging the respective first and second contact faces of the spindle.

12. The surgical lighting system of claim 5, wherein the spindle includes an arcuate tab, and the first and second contact faces of the spindle are on opposite sides of the arcuate tab.

13. The surgical lighting system of claim 12, wherein the arcuate tab of the spindle protrudes radially outward.

14. The surgical lighting system of claim 5, wherein the camera assembly includes a protruding member, and wherein the first rotation range is defined by opposite sides of the protruding member engaging the respective first and second contact faces of the free rotating ring.

15. The surgical lighting system of claim 14, wherein the protruding member includes a screw threaded into a wall of the bracket of the camera assembly, and the screw protrudes radially inward.

16. The surgical lighting system of claim 15, wherein the free rotating ring includes a first arcuate tab, and the first and second contact faces of the free rotating ring are on opposite sides of the first arcuate tab.

17. The surgical lighting system of claim 16, wherein the first arcuate tab of the free rotating ring protrudes radially outward.

18. The surgical lighting system of claim 17, wherein the protruding portion of the free rotating ring includes a second arcuate tab, and wherein the second rotation range is defined by opposite faces of the second arcuate tab engaging the respective first and second contact faces of the spindle.

19. The surgical lighting system of claim 18, wherein the second arcuate tab protrudes radially inward.

20. The surgical lighting system of claim 5, wherein the spindle includes an arcuate cutout, wherein opposite faces of the arcuate cutout form the respective first and second contact faces of the spindle.

21. The surgical lighting system of claim 3, further comprising a motor coupled to the bracket to rotate the bracket.

22. The surgical lighting system of claim 21, wherein the motor is mounted within the handle housing and is fixed relative to the spindle.

23. The surgical lighting system of claim 3, wherein the spindle is a hollow cylindrical spindle that has an inner and outer circumference and the inner circumference is continuous.

24. The surgical lighting system of claim 1, wherein the camera outputs an optical video signal.

25. A method of rotating a camera of a surgical lighting system, comprising:
- positioning a light head housing including a plurality of light emitting elements therein that are arranged to emit light downward to a region of interest;
- gripping a handle mounted to the light head housing and protruding downward from the light head housing, the handle including a handle housing having a sufficient size to be gripped by a human hand; and,
- rotating a camera assembly mounted within the handle housing, the camera assembly including a camera having a field of view that encompasses at least a portion of the region of interest;
- wherein rotating the camera assembly includes rotation within the handle housing greater than 360 degrees about a rotation axis from a first stop to a second stop and vice versa, wherein the first stop limits clockwise rotation of the camera about the rotation axis and the second stop limits counterclockwise rotation of the camera about the rotation axis.

26. A surgical lighting system, comprising:
- a light head housing including a plurality of light emitting elements therein that are arranged to emit light downward to a region of interest;
- a handle mounted to the light head housing and protruding downward from the light head housing, the handle including a handle housing having a sufficient size to be gripped by a human hand; and,
- a camera assembly mounted within the handle housing, the camera assembly including a camera having a field of view that encompasses at least a portion of the region of interest;
- wherein the camera assembly is mounted within the handle housing for rotation greater than 360 degrees about a rotation axis from a first stop to a second stop and vice versa, wherein the first stop limits clockwise rotation of the camera about the rotation axis and the second stop limits counterclockwise rotation of the camera about the rotation axis;
- wherein the camera assembly includes a bracket that is rotatably mounted to a spindle fixed relative to the handle housing.

* * * * *